United States Patent
Kubota et al.

(12) 
(10) Patent No.: US 6,627,654 B2
(45) Date of Patent: Sep. 30, 2003

(54) ANTHROPOD-CONTROLLING COMPOSITION

(75) Inventors: Shunichi Kubota, Minoo (JP); Michihiko Fujinami, Minoo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/832,092

(22) Filed: Apr. 11, 2001

(65) Prior Publication Data

US 2001/0049389 A1 Dec. 6, 2001

(30) Foreign Application Priority Data

Apr. 25, 2000 (JP) ........................................ 2000-123982

(51) Int. Cl.[7] ............................................... A01N 43/16
(52) U.S. Cl. ..................... 514/460; 514/875; 514/876; 514/919; 424/DIG. 10; 424/DIG. 11
(58) Field of Search ................................. 514/460, 919, 514/875, 876; 424/DIG. 10, DIG. 11

(56) References Cited

FOREIGN PATENT DOCUMENTS

| | | |
|---|---|---|
| EP | 0 841 063 | 5/1998 |
| JP | 50-24436 A | 3/1975 |
| JP | 51-19126 | 2/1976 |
| JP | 10-120519 | 5/1988 |
| JP | 7-126110 | 5/1995 |
| JP | 10-130114 | 5/1998 |
| WO | WO 88/10258 | 12/1988 |

OTHER PUBLICATIONS

CABA Abstract 93:103752 (1993).*
CAPLUS abstract 1969 : 470444 [Chemical Abstracts 71:70444], 1969.*
*Tetrahedron Letters*, vol. 27, Pergamon Press. Printed in Great Britian, 1969, pp. 2279–2280.
Chemical Abstracts, absract No. 100:180061, vol. 15, No. 3, 1984, pp. 112–113.
Amateur Aromatherapy—Oil Database @ http://www.andy-barson.binternet.co.uk/oildata.htm (Date Unavailable).
de Rijke et al., "Acidic Components in Essential Oils of Costus Root, Patchouli and Olibanum", *Phytochemistry*, vol. 17, 1978, pp. 1666–1667.
Nakahara et al., "Acidic Compounds in Patchouli Oil", *Phytochemistry*, vol. 14, 1975, pp. 2713–2714.

* cited by examiner

Primary Examiner—John Pak
(74) Attorney, Agent, or Firm—Sughrue Mion, PLLC

(57) ABSTRACT

Arthropod-controlling composition comprising an α-pyrone compound shown by the formula:

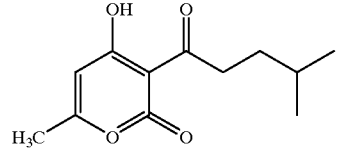

as an active ingredient provides an excellent activity for controlling arthropods, and therefore, the composition is utilized for controlling harmful arthropods.

13 Claims, No Drawings

ANTHROPOD-CONTROLLING COMPOSITION

FIELD OF THE INVENTION

The present invention relates to an arthropod-controlling composition comprising a specific α-pyrone compound as an active ingredient.

BACKGROUND ART

Many arthropod-controlling compositions are on the market at present. However, the objected harmful arthropods have many kinds and the situations for controlling them are in many ways. Therefore, the arthropod-controlling composition having practically high effectiveness and safety is desired.

Though pyrethroid pesticides having rapid knock-down efficacy are excellent agents for controlling harmful insects, progress of pyrethroid resistance to some insects has been reported in various places recently. Under these circumstances, non-pyrethroid compounds having excellent knock-down efficacy are earnestly desired.

On the other hand, it is known that some α-pyrone compounds are effective for controlling harmful acarina and insects such as housefly in Japanese Unexamined Patent Publication No. sho-51-19126. However, the compounds described in the publication do not necessarily give a sufficient effect.

SUMMARY OF THE INVENTION

The present invention provides an arthropod-controlling composition comprising an α-pyrone compound (hereinafter, referred to as the Pyrone Compound) shown by formula:

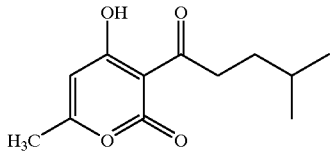

as an active ingredient, and the composition has an extremely high knock-down activity against harmful arthropods.

DISCLOSURE OF THE INVENTION

Examples of the arthropods against which the arthropod-controlling composition of the present invention exhibits a controlling effect include the following harmful insects, acarina, Diplopoda, Chilopoda and Isopoda:

Hemiptera:
   Delphacidae (planthoppers) such as *Laodelphax striatellus* (small brown planthopper), *Nilaparvata lugens* (brown planthopper) and *Sogatella furcifera* (white-backed rice planthopper); Deltocephalidae (leafhoppers) such as *Nephotettix cincticeps* (green rice leafhopper), *Recilia dorsalis* (zig-zag rice leaf hopper) and *Nephotettix virescens* (green rice leafhopper), Aphididae (aphids) such as cotton aphid (*Aphis gossypii*); stink bugs; Aleyrodidae (whiteflies) such as *Bemisia argentifolii*; scales; Tingidae (lace bugs); Psyllidae (suckers) and so on.

Lepidoptera:
   Pyralidae such as *Chilo suppressalis* (rice stem borer), *Cnaphalocrocis medinalis* (rice leafroller) and *Plodia interpunctella* (Indian meal moth); Noctuidae such as *Spodoptera litura* (tobacco cutworm), *Pseudaletia separata* (rice armyworm), *Mamestra brassicae* (cabbage armyworm), Agrotis spp. (e.g. *Agrotis segetum* (turnip cutworm), *Agrotis ipsilon* (black cutworm)), Helicoverpa spp., Heliothis spp. and Plusiinae; Pieridae such as *Pieris rapae crucivora* (common cabbageworm); Tortricidae such as Adoxophyes spp. (e.g. *Adoxophyes orana fasciata*); Carposinidae such as *Carposina niponensis* (peach fruit moth); Lyonetiidae; Lymantriidae; Plutellidae such as *Plutella xylostella* (diamondback moth); Hesperiidae such as *Parnara guttata* (rice skipper); Tineidae such as *Tinea pellionella* (casemaking clothes moth) and *Tineola bisselliella* (webbing clothes moth) and so on.

Diptera:
   Culicidae (mosquitoes) such as Culex spp. (e.g. *Culex pipiens pallens* (common mosquito), *Culex tritaeniorhynchus*), Aedes spp. (e.g. *Aedes aegypti* (yellow fever mosquito), *Aedes alhopictus*) and Anopheles spp. (e.g. *Anopheles sinensis*); Chironomidae (midges); Muscidae such as *Musca domestica* (housefly), *Muscina stabulans* (false stablefly) and *Fannia canicularis* (little housefly); Calliphoridae; Sarcophagidae; Anthomyiidae such as *Delia platura* (seedcorn maggot) and *Delia antiqua* (onion maggot); Tephritidae (fluit flies); Drosophilidae; Psychodidae (moth flies); Tabanidae; Simuhidae (black flies); Stomoxyidae; Phoridae; Ceratopogonidae (biting midges) and so on.

Coleoptera (Beetles):
   Scarabaeidae (scarabs) such as *Anomala cuprea* (cupreous chafer) and *Anomala rufocuprea* (soybean beetle); Curculionidae (weevils) such as *Sitophilus zeamais* (maize weevil), *Lissorhoptrus oryzophilus* (ricewater weevil), ball weevil and *Callosobruchus chinensis* (adzuki bean weevil); Dermestidae such as *Authrenus verbasci* (varied carpet beetle) and *Attagenus unicolor japonicus* (black carpet beetle); Tenebrionidae (darkling beetles) such as *Tenebrio molitor* (yellow mealworm) and *Triboium castaneum* (red flour beetle); Chrysomelidae (leaf beetles) such as *Oulema oryzae* (rice leaf beetle), *Phyllotreta striolata* (striped flea beetle) and *Aulacophora femoralis* (cucurbit leaf beetle); Corn rootworms such as *Diabrotica virgifera* (western corn rootworm) and *Diabrotica undecimpunctata howardi* (southern corn rootworm); Anobiidae; Coccinellidae (ladybirds) such as Epilachna spp. (e.g. *Epilachna vigintioctopunctata* (twenty-eight-spotted ladybird)); Lyctidae (powderpost beetles); Bostrychidae (false powderpost beetles); Cerambycidae; Staphylinidae such as *Paederus fuscipes* (robe beetle) and so on.

Dictyoptera:
   *Blattella germanica* (German cockroach); *Periplaneta fuliginosa* (smokybrown cockroach); *Periplaneta americana* (American cockroach); *Periplaneta brunnea* (brown cockroach); *Blatta orientalis* (oriental cockroach) and so on;

Thysanoptera (Thrips):
   *Thrips palmi*, western flower thrips, *Thrips hawaiiensis* (flower thrips) and so on.

Hymenoptera:
   Formicidae (ants) such as *Formica japonica*, field ant (*Lasius fuliginosus*), little red ant (*Monomorium pharaonis*), little ant (*Monomorium nipponensis*) and pavement ant (*Teramorium caespitum*); Vespidae (hornets); Polistes spp. (long-legged wasps); Bethylidae; Tenthredinidae (sawflies) such as *Athalis rosae ruficornis* (cabbage sawfly) and so on.

Orthoptera:
   Gryllotalpidae (mole crickets); Acrididae (grasshoppers) and so on.

Siphonaptera Pests (Fleas):
  *Ctenocephalides canis* (dog flea); *Ctenocephalides felis* (cat flea); *Pulex irritans* and so on.
Anoplura (Lice):
  *Pediculus corporis; Pediculus humanus* (body louse); *Pthirus pubis* (crab louse) and so on.
Isoptera:
  *Reticulitermes speratus; Coptotermes formosanus* and so on.
Tetranychidae (Spider Mites):
  *Tetranychus cinnabarinus* (carmine spider mite); *Tetranychus urticae* (two-spotted spider mite); *Tetranychus kanzawai* (Kanzawa spider mite); *Panonychus citri* (citrus red mite); *Panonychus ulmi* (European red mite) and so on.
Ixodidae:
  *Boophilus microplus; Haemaphysalis longiconis* and so on
House-Dust Mites:
  Acaridae such as *Tyrophagus putrescentiae* (copra mite) and *Aleuroglyphus ovatus* (brown legged grain mite); Dermanyssidae such as *Dermatophagoides farinae* (American house dust mite) and *Dermatophagoides pteronyssinus*; Glycyphagidae such as *Glycyphagus privatus, Glycyphagus domesticus* and *Glycyphagus destructor*; Cheyletidae such as *Chelacaropsis malaccensis* and *Cheyletus fortis*; Tarsonemidae; Chortoglyphus spp.; Haplochthonius spp. and so on.
Diplopoda (Milpedes):
  Chilognatha such as Oxydus spp. and so on.
Chilopoda (Centipedes):
  *Scolopendra suhspinipes mutilans*, red centipede and so on.
Isopoda:
  Oniscoidea (pill bugs) such as Porcellio spp. (e.g. *Porcellio scaber*), Porcellionides spp. and Armadillidium spp. (e.g. *Armadillium vulgare*) and so on.

The Pyrone Compound can be prepared according to the procedure below:
Preparation of the Pyrone Compound
  Ten grams (10.0 g, 79.3 mmol) of 4-hydroxy-6-methyl-2-pyrone were suspended in 100 ml of toluene at room temperature. To the suspension, 1.22 g (10.0 mmol) of N,N-dimethylaminopyridine, 10.0 g (86.1 mmol) of isocaproic acid and 18.5 g (89.7 mmol) of dicyclohexylcarbodiimide were added subsequently. The mixed solution was stirred for one hour at room temperature, and then heated to 70° C. and stirred for 20 hours under heating. After the mixed solution was allowed to stand at room temperature, the precipitated insoluble dicyclohexylurea was filtered off, and washed with 1N hydrochloric acid once and 10% (by weight) brine twice. The organic layer collected from the filtrate was dried over anhydrous magnesium sulfate and evaporated under reduced pressure to give a crude oily product.
  The oily product was subjected to silica gel column chromatography (eluent: hexane/ethyl acetate=6/1) to give 7.11 g of the Pyrone Compound (yield 40%).
  $^1$H-NMR (CDCl$_3$/TMS): 0.94 (6H, d), 1.54 (2H, q), 1.63 (1H, m), 2.27 (3H, s), 3.08 (2H, t), 5.93 (1H, s), 17.88 (1H, s)
  The Pyrone Compound utilized in the present invention is a compound of formula:

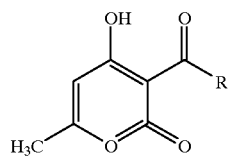

wherein R represents a group of —CH$_2$CH$_2$CH(CH$_3$)$_2$, having an NMR spectrum described above and melting point of 42° C.

The arthropod-controlling composition of the present invention comprises the Pyrone Compound as an active ingredient and an inert carrier. The content of the Pyrone Compound in the arthropod-controlling composition is an effective amount, usually 0.001 to 95% by weight. The arthropod-controlling composition is usually to be formulated as described below for use.

The Pyrone Compound can be formulated to the present composition such as oil solution, emulsifiable concentrate, wettable powder, flowable (aqueous suspension or aqueous emulsion), granule, dust and so on, by mixing with solid carrier, liquid carrier or gaseous carrier and optionally surfactant, the other formulation additive.

Examples of the solid carrier used in the formulation described above include inorganic carriers such as clays (e.g. kaolin clay, diatomaceous earth, synthetic hydrated silicon oxide, bentonite, Fubasami clay, acid clay), talc, ceramics, sericite, quartz and calcium carbonate. Examples of the liquid carrier include water, alcohols (e.g. methanol, ethanol, higher alcohols), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosine, gas oil), esters (ethyl acetate, butyl acetate), nitrites (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethyl sulfoxide and vegetable oils (e.g. soybean oil, cottonseed oil). Examples of the liquefied gaseous carrier include fluorocarbon, fluorohydrocarbon, LPG (liquefied petroleum gas), dimethyl ether and carbon dioxide.

Examples of the surfactant optionally used in the formulation include alkyl sulfate salts, alkylsulfonate salts, alkylarylsulfonate salts, alkyl aryl ethers, polyoxyethylenealkyl aryl ethers, polyethylene glycol ethers, polyhydric alcohol esters and sugar alcohol derivatives.

The other formulation auxiliaries are exemplified by sticking agent, dispersant and stabilizer. Examples of sticking agent and dispersant include casein, gelatin, polysaccharides (e.g. starch powder, gum arabic, cellulose derivatives, alginic acid), lignin derivatives, bentonite, sugars and synthetic water-soluble polymers (e.g. polyvinyl alcohol, polyvinylpyrrolidone, polyacrylic acids). Examples of stabilizer include phenol type antioxidants such as BHT (2,6-di-tert-butyl-4-methyphenol) and BHA (mixture of 2-tert-butyl-4-methoxyphenol and 3-tert-butyl-4-methoxyphenol), amine type antioxidants such as diphenylamine, organic sulfur type antioxidants such as 2-mercaptobenzimidazole, PAP (acid isopropyl phosphate), vegetable oils, mineral oils, surfactants, fatty acids and esters of fatty acid.

The flowable formulations (aqueous suspension or aqueous emulsion) usually comprise the Pyrone Compound, dispersant, suspension assistant (for example, protective colloid or a compound giving thixotropy), suitable auxiliaries (for example, antifoamer, rust preventive agent, stabilizer, developing agent, penetrating assistant, antifreezing agent, bactericide, fungicide, etc.) and water. Examples of the protective colloid include gelatin, casein, gums, cellulose ethers and polyvinyl alcohol, and examples of the compound giving thixotropy include bentonite, aluminum magnesium silicate, xanthan gum and polyacrylic acids. Use of the oil which can rarely dissolve the Pyrone Compound in place of water can give suspension-in-oil formulation.

The formulations of emulsifiable concentrate, wettable powder, flowable and so on obtained above are usually diluted with water and so on, and applied at 0.1 to 10000 ppm of the concentration of the Pyrone Compound. The formulations of oil solution, granule, dust and so on are usually applied as they are.

Further, the Pyrone Compound or its formulation can be used after making the forms below.

A mixture of the Pyrone Compound or its liquid formulation and a propellant can be charged into a pressure container with a spray nozzle to afford an aerosol of the present controlling agent. Further, the Pyrone Compound or its liquid formulation can be impregnated into a base material of mosquito-coil, mosquito-mat, ceramic board and so on to afford a heating volatile formulation such as mosquito-coil and mosquito-mat for electric heater; a heating fumigant formulation such as self-combustible fumigant, chemical reaction type fumigant and porous ceramic board fumigant; a non-heating volatile formulation such as resin volatile formulation and paper volatile formulation; a smoking formulation such as fogging; and an ULV formulation of the present controlling agent. Furthermore, a liquid formulation of the Pyrone Compound can be charged into a container with an absorptive wick in the upper part to afford a bottle containing insecticidal liquid for volitilization by heating the absorptive wick.

Examples of the propellant for aerosols include propane, butane, isobutane, dimethyl ether, methyl ethyl ether and methylal.

An example of the base material of the mosquito-coil is a mixture of raw plant powder such as wood powder and Pyrethrum marc and a binding agent like Tabu powder (powder of *Machilus thunbergii*), starch or gluten.

Examples of the base material of the mosquito-mat for electric heating fumigation include a plate of compacted fibrils of cotton linters and a mixture of pulp and cotton linters.

The base material of the self-combustible fumigant includes, for example, an exothermic agent (e.g. nitrate, nitrite, guanidine salt, potassium chlorate, nitrocellulose, ethylcellulose, wood powder), a pyrolytic stimulating agent (e.g. alkali metal salt, alkaline earth metal salt, dichromate, chromate), an oxygen source (e.g. potassium nitrate), a combustion assistant (e.g. melanin, wheat starch), a bulk filler (e.g. diatomaceous earth) and a binding agent (e.g. synthetic glue).

The base material of the chemical reaction type fumigant includes, for example, an exothermic agent (e.g. alkali metal sulfide, polysulfide, hydrogensufide and hydrated salt, calcium oxide), a catalytic agent (e.g. carbonaneous substance, iron carbide, activated clay), an organic foaming agent (e.g. azodicarbonamide, benzenesulfonylhydrazide, dinitrosopentamethylenetetramine, polystyrene, polyurethane, etc.) and a filler (e.g. natural or synthetic fibers).

An example of the base material of the resin volatile formulation is thermoplastic resin, and examples of the base material of the paper volatile formulation include filter paper and Japanese paper.

The present arthropod-controlling composition can be used simultaneously with the other insecticide, the other acaricide, repellent or synergist under non-mixed conditions or pre-mixed conditions.

Examples of the insecticides and acaricides include organophosphorus compounds such as fenitrothion [O,O-dimethyl O-(3-methyl-4-nitrophenyl) phosphorothioate], fenthion [O,O-dimethyl O-(3-methyl-4-(methythio)phenyl) phosphorothioate], diazinon [O,O-diethyl O-2-isopropyl-6-methylpyrimidin-4-yl phosphorothioate], chlorpyrifos [O,O-diethyl O-3,5,6-trichloro-2-pyridyl phosphorothioate], DDVP [2,2-dichlorovinyl dimethyl phosphate], cyanophos [O-4-cyanophenyl O,O-dimethyl phosphorothioate], dimethoate [O,O-dimethyl S-(N-methylcarbamoylmethyl) dithiophosphate], phenthoate [ethyl 2-dimethoxyphosphinothioylthio(phenyl)acetate], malathion [diethyl (dimethoxyphosphinothioylthio) succinate], and azinphos-methyl [S-3,4-dihydro-4-oxo-1,2,3-benzotriazin-3-ylmethyl O,O-dimethyl phosphorodithioate]; carbamate compounds such as BPMC (2-sec-butylphenyl methylcarbamate), benfracarb [ethyl N-[2,3-dihydro-2,2-dimethylbenzofuran-7-yloxycarbonyl (methyl)aminothio]-N-isopropyl-β-alaninate], propoxur [2-isopropoxyphenyl N-methylcarbamate] and carbaryl [1-naphthyl-N-methylcarbamate], methomyl [S-methyl-N-[(methylcarbamoyl)oxy]thioacetimidate]; pyrethroid compounds such as etofenprox [2-(4-ethoxyphenyl)-2-methylpropyl-3-phenoxybenzyl ether], fenvalerate [(RS)-α-cyano-3-phenoxybenzyl (RS)-2-(4-chlorophenyl)-3-methylbutyrate], esfenvalerate [(S)-α-cyano-3-phenoxybenzyl (S)-2-(4-chlorophenyl)-3-methylbutyrate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS)-cis,trans-3-(2,2-dichlorovinyl)-2,2-dimethylcyclopropanecarboxylate], permethrin [3-phenoxybenzyl (1RS)-cis,trans-3-(2,2-dichlorovinyl)-2,2-dimethylcyclopropanecarboxylate], cyhalothrin [(RS)-α-cyano-3-phenoxybenzyl (Z)-(1RS)-cis-3-(2-chloro-3,3,3-trifluoroprop-1-enyl)-2,2-dimethylcyclopropanecarboxylate], deltamethrin [(S)-α-cyano-3-phenoxybenzyl (1R)-cis-3-(2,2-dibromovinyl)-2,2-dimethylcyclopropanecarboxylate], cycloprothrin [(RS)-α-cyano-3-phenoxybenzyl (RS)-2,2-dichloro-1-(4-ethoxyphenyl)cyclopropanecarboxylate], fluvalinate [α-cyano-3-phenoxybenzyl N-(2-chloro-α,α,α-trifluoro-p-tolyl)-D-valinate], bifenthrin [2-methylbiphenyl-3-ylmethyl (Z)-(1RS)-cis-3-(2-chloro-3,3, 3-trifluoroprop-1-enyl)-2,2-dimethylcyclopropanecarboxylate], 2-methyl-2-(4-bromodifluoromethoxyphenyl)propyl 3-phenoxybenzyl ether, tralomethrin [(S)-α-cyano-3-phenoxybenzyl (1R-cis)-3-{(1RS)(1,2,2,2-tetrabromoethyl)}-2,2-dimethylcyclopropanecarboxylate], silafluofen [(4-ethoxyphenyl){3-(4-fluoro-3-phenoxyphenyl)propyl}dimethylsilane], d-phenothrin [3-phenoxybenzyl (1R-cis,trans)-chrysanthemate], cyphenothrin [(RS)-α-cyano-3-phenoxybenzyl (1R-cis,trans)-chrysanthemate], d-resmethrin [5-benzyl-3-furylmethyl (1R-cis,trans)-chrysanthemate], acrinathrin [(S)-α-cyano-3-phenoxybenzyl (1R,cis(Z))-2,2-dimethyl-3-{3-oxo-3-(1,1,1,3,3,3-hexafluoropropyloxy) propenyl}cyclopropanecarboxylate], cyfluthrin [(RS)-α-cyano-4-fluoro-3-phenoxybenzyl 3-(2,2-dichlorovinyl)-2,2-dimethylcyclopropanecarboxylate], tefluthrin [2,3,5,6-tetrafluoro-4-methylbenzyl (1RS-cis(Z))-3-(2-chloro-3,3,3-trifluoroprop-1-enyl)-2,2-dimethylcyclopropanecarboxylate], transfluthrin [2,3,5,6-tetrafluorobenzyl (1R-trans)-3-(2,2-dichlorovinyl)-2,2-dimethylcyclopropanecarboxylate], tetramethrin [3,4,5,6-tetrahydrophthalimidomethyl (1RS)-cis,trans-chrysanthemate], allethrin [(RS)-3-allyl-2-methyl-4-oxocyclopent-2-enyl (1RS)-cis,trans-chrysanthemate], prallethrin [(S)-2-methyl-4-oxo-3-(2-propynyl)cyclopent-2-enyl (1R)-cis,trans-chrysanthemate], empenthrin [(RS)-1-ethynyl-2-methyl-2-pentenyl (1R)-cis, trans-chrysanthemate], imiprothrin [2,5-dioxo-3-(prop-2-ynyl)

imidazolidin-1-ylmethyl (1R)-cis,trans-2,2-dimethyl-3-(2-methylprop-1-enyl)cyclopropanecarboxylate], d-furamethrin [5-(2-propynyl)furfuryl (1R)-cis,trans-chrysanthemate] and 5-(2-propynyl)furfuryl 2,2,3,3-tetramethylcyclopropanecarboxylate; nitroimidazoliiine derivatives such as imidacioprid (1-(6-chloro-3-pyridylmethyl)-N-nitroimidazolidin-2-ylideneamine); N-cyanoamidine derivatives such as N-cyano-N'-methyl-N'-(6-chloro-3-pyridylmethyl)acetamidine; nitenpyram [N-(6-chloro-3-pyridylmethyl)-N-ethyl-N-methyl-2-nitrovynylidenediamine]; thiacloprid [1-(2-chloro-5-pyridylmethyl)-2-cyanoiminothiazoline]; thiamethoxam [3-((2-chloro-5-thiazolyl) methyl)-5-methyl-4-nitroiminotetrahydro-1,3,5-oxadiazine]; 1-methyl-2-nitro-3-((3-tetrahydrofuryl)methyl)guanidine; 1-(2-chloro-5-thiazolyl)methyl-3-methyl-2-nitroguanidine; nitroiminohexahydro-1,3,5-triazine derivatives; chlorinated hydrocarbons such as endosulfan [6,7,8,9,10,10-hexachloro-1,5,5a,6,9,9a-hexahydro-6,9-methano-2,4,3-benzodioxathiepine oxide], γ-BHC [1,2,3,4,5,6-hexachlorocyclohexane] and 1,1-bis(chlorophenyl)-2,2,2-trichloroethanol; benzoylphenylurea compounds such as chlorfluazuron [1-(3,5-dichloro-4-(3-chloro-5-trifluoromethylpyridyn-2-yloxy)phenyl)-3-(2,6-difluorobenzoyl)urea], teflubenzuron [1-(3,5-dichloro-2,4-difluorophenyl)-3-(2,6-difluorobenzoyl)urea] and flufenoxuron [1-(4-(2-chloro-4-trifluoromethylphenoxy)-2-fluorophenyl)-3-(2,6-difluorobenzoyl)urea]; juvenile hormone like compounds such as pyriproxyfen [4-phenoxyphenyl 2-(2-pyridyloxy)propyl ether], methoprene [isopropyl (2E,4E)-11-methoxy-3,7,11-trimethyl-2,4-dodecadienoate] and hydroprene [ethyl (2E,4E)-11-methoxy-3,7,11-trimethyl-2,4-dodecadienoate]; thiourea derivatives such as diafenthiuron [N-(2,6-diisopropyl-4-phenoxyphenyl)-N'-tert-butylcarbodiimide]; phenylpyrazole compounds; 4-bromo-2-(4-chlorophenyl)-1-ethoxymethyl-5-trifluoromethylpyrrol-3-carbonitrile [chlorfenapil]; metoxadiazone [5-methoxy-3-(2-methoxyphenyl)-1,3,4-oxadiazol-2(3H)-one], bromopropylate [isopropyl 4,4-dibromobenzilate], tetradifon [4-chlorophenyl 2,4,5-trichlorophenyl sulfone], chinomethionat [S,S-6-methylquinoxaline-2,3-diyldithiocarbonate], pyridaben [2-tert-butyl-5-(4-tert-butylbenzylthio)-4-chloropyridazin-3(2H)-one], fenpyroximate [tert-butyl (E)-4-[(1, 3-dimethyl-5-phenoxypyrazol-4-yl) methyleneaminooxymethyl]benzoate], tebufenpyrad [N-(4-tert-butylbenzyl)-4-chloro-3-ethyl-1-methyl-5-pyrazolecarboxamide], polynactins complex [tetranactin, dinactin and trinactin], pyrimidifen [5-chloro-N-[2-{4-(2-ethoxyethyl)-2,3-dimethylphenoxy}ethyl]-6-ethylpyrimidin-4-amine], milbemectin, abamectin, ivermectin and azadirachtin [AZAD]. Examples of the repellants include 3,4-carane-diol, N,N-diethyl-m-toluamide, 1-methylpropyl 2-(2-hydroxyetnyl)-1-piperidinecarboxylate, p-menthane-3,8-diol and plant essential oil such as hyssop oil, and examples of the synergists include bis-(2,3,3,3-tetrachloropropyl) ether (S-421), N-(2-ethylhexyl)bicyclo[2.2.1]hept-5-ene-2,3-dicarboximide (MGK-264) and α-[2-(2-butoxyethoxy)ethoxy]-4,5-methylenedioxy-2-propyltoluene (piperonyl butoxide).

The application amount and concentration of the present controlling agent can be suitably designed according to the type of the formulations, time, place, and method of application, kind of harmful arthropods and damage.

The present compound can exhibit its more excellent pesticidal effect under heating or non-heating volatilation. Therefore, it is especially useful as an active ingredient of household pesticide.

EXAMPLES

The present invention will be further illustrated in more details by the preparation examples and test examples, although the present invention is not limited in any sense to these examples. Parts represent parts by weight in the following examples.

Preparation Example 1

Twenty parts of the Pyrone Compound are dissolves in 65 parts of xylene, mixed with 15 parts of Sorpol 3005X (surfactant, registered trademark of Toho Chemical Co., Ltd.), and stirred sufficiently to give 20% emulusifiable concentrate.

Preparation Example 2

Ten parts of the Pyrone Compound are dissolves in a mixture of 35 parts of xylene and 35 parts of N,N-dimethylformamide. Twenty parts of Sorpol 3005X (surfactant, registered trademark of Toho Chemical Co., Ltd.) are added thereto and stirred sufficiently to give 10% emulusifiable concentrate.

Preparation Example 3

Forty parts of the Pyrone Compound are mixed first with 5 parts of Sorpol 5060 (surfactant, registered trademark of Toho Chemical Co., Ltd.) and then with 32 parts of Carplex #80 (registered trademark of Shionogi & Co., Ltd.; fine powder of synthetic hydrated silicon oxide) and 23 parts of 300-mesh diatomaceous earth, and stirred with a juice mixer to give 40% wettable powder.

Preparation Example 4

One and a half parts (1.5 parts) of the Pyrone Compound are mixed with 98.5 parts of AGSORB LVM-MS 24/48 (granular carrier of calcined montmorillonite having the particle diameter of 24- to 48-mesh provided by OIL DRI Corp.) sufficiently to give 1.5% granule.

Preparation Example 5

A mixture of 10 parts of the Pyrone Compound, 10 parts of phenylxylylethane and 0.5 part of Sumidule L-75 (tolylenediisocyanate provided by Sumika-Bayer Urethane Co., Ltd.) is added to 20 parts of a 10% aqueous solution of gum arabic, and stirred with a homomixer to give an emulsion having the mean particle diameter of 20 μm. The emulsion is further mixed with 2 parts of ethylene glycol and allowed to react on a water bath of 60° C. for 24 hours to give a microcapsule slurry.

A thicking agent solution is prepared by dispersing 0.2 part of xanthan gum and 1.0 part of Veegum R (aluminum magnesium silicate provided by Sanyo Chemical Co., Ltd.) in 56.3 parts of ion-exchanged water.

Forty-two and a half (42.5) parts of the above microcapsule slurry and 57.5 parts of the above thicking agent solution are mixed to give 10% microencapsulated formulation.

Preparation Example 6

A mixture of 10 parts of the Pyrone Compound and 10 parts of phenylxylylethane is added to 30 parts of a 10% (by weight) aqueous solution of polyvinyl alcohol and stirred with a homomixer to give an emulsion having the mean particle diameter of 3 μm.

A thicking agent solution is prepared by dispersing 0.2 part of xanthan gum and 0.4 part of Veegum R (aluminum magnesium silicate provided by Sanyo Chemical Co., Ltd.) in 49.4 parts of ion-exchanged water.

Fifty parts of the above emulsion and 50 parts of the above thicking agent solution are mixed to give 10% flowable formulation.

Preparation Example 7

Ten parts of the Pyrone Compound, 17.5 parts of ammonium polyoxyethylene alkyl ether sulfate, 17.5 parts of white carbon and 55 parts of water are mixed and pulverized well by wet grinding to give 10% flowable formulation.

Preparation Example 8

Five parts of the Pyrone Compound are mixed with 3 parts of Carplex #80 (registered trademark of Shionogi & Co., Ltd.; fine powder of synthetic hydrated silicon oxide), 0.3 parts of PAP and 91.7 parts of 300-mesh talc, and stirred with a juice mixer to give 5% dust.

Preparation Example 9

A half part (0.5 part) of the Pyrone Compound is dissolved in 10 parts of dichloromethane and mixed with 89.5 parts of Isoper M (isoparaffin provided by Exxon Chemical Corp.) to give 0.5% oil solution.

Preparation Example 10

An aerosol vessel is filled with 0.1 g of the Pyrone Compound and 49.9 g of Neotiozol (Chuokasei Company). The vessel is then equipped with a valve, and 25 g of dimethyl ether and 25 g of LPG are charged and shaken. The aerosol vessel is equipped with an actuator and to give oil-based aerosol.

Preparation Example 11

An aerosol vessel is filled with 0.2 g of the Pyrone Compound and 49.8 g of Neotiozol (Chuokasei Company). The vessel is then equipped with a valve, and 25 g of dimethyl ether and 25 g of LPG are charged and shaken. The aerosol vessel is equipped with an actuator and to give oil-based aerosol.

Preparation Example 12

An aerosol vessel is filled with 0.4 g of the Pyrone Compound and 49.6 g of Neotiozol (Chuokasei Company). The vessel is then equipped with a valve, and 25 g of dimethyl ether and 25 g of LPG are charged and shaken. The aerosol vessel is equipped with an actuator and to give oil-based aerosol.

Preparation Example 13

An aerosol vessel is filled with 0.8 g of the Pyrone Compound and 49.2 g of Neotiozol (Chuokasei Company). The vessel is then equipped with a valve, and 25 g of dimethyl ether and 25 g of LPG are charged and shaken. The aerosol vessel is equipped with an actuator and to give oil-based aerosol.

Preparation Example 14

An aerosol vessel is filled with 1.6 g of the Pyrone Compound and 48.4 g of Neotiozol (Chuokasei Company). The vessel is then equipped with a valve, and 25 g of dimethyl ether and 25 g of LPG are charged and shaken. The aerosol vessel is equipped with an actuator and to give oil-based aerosol.

Preparation Example 15

An aerosol vessel is filled with 50 parts of purified water and a dissolved mixture of 0.6 part of the Pyrone Compound, 0.01 part of BHT, 5 parts of xylene, 3.39 parts of deodorized kerosine and 1 part of Atmos 300 (registered trademark of Atlas Chemical Co.). The vessel is then equipped with a valve and 40 parts of propellant (liquefied petroleum gas) is charged through the valve into the aerosol vessel under pressure to give water-based aerosol.

Preparation Example 16

An aerosol vessel is filled with 1.12 g of the Pyrone Compound and 11.38 g of Isoper M (isoparaffin produced by Exxon Chemical Corp.). The vessel is equipped with a valve, and then 37.5 g of dimethyl ether and 12.5 g of LPG (liquefied petroleum gas) are charged through the valve into the aerosol vessel. After shaking, an actuator for total-release aerosol is equipped to give total-release aerosol.

Preparation Example 17

A solution prepared by dissolving 0.5 g of the Pyrone Compound in 20 ml of acetone is homogeneously mixed with 99.5 g of a carrier for a mosquito-coil (mixture of Tabu powder, Pyrethrum marc and wood powder at the ratio of 4:3:3). After 120 ml of water is added, the mixture is kneaded sufficiently, molded and dried to give mosquito-coil.

Preparation Example 18

One hundred and twenty grams (120 g) of water dissolving 0.3 g of Malachite Green and 0.2 g of sodium dehydroacetate are added to a carrier for a mosquito-coil (mixture of Tabu powder, Pyrethrum marc and wood powder at the ratio of 5:3:2), kneaded sufficiently, molded and dried to give a base material for mosquito-coil. One hundred milligrams (100 mg) of the Pyrone Compound are dissolved in 5 ml of acetone. A quarter milliliter (0.25 ml) of the solution is painted on 0.5 g of the above base material for mosquito-coil and sufficiently air-dried to give 1% mosquito-coil.

Preparation Example 19

One hundred and twenty grams (120 g) of water dissolving 0.3 g of Malachite Green and 0.2 g of sodium dehydroacetate are added to a carrier for a mosquito-coil (mixture of Tabu powder, Pyrethrum marc and wood powder at the ratio of 5:3:2), kneaded sufficiently, molded and dried to give a base material for mosquito-coil. In 0.7 g of deodorized kerosene, 0.3 g of the Pyrone Compound is dissolved. One gram (1 g) of the solution is painted on 29 g of the above base material for mosquito-coil and sufficiently air-dried to give 1% mosquito-coil.

Preparation Example 20

A solution prepared by dissolving 1 g of the Pyrone Compound in 20 ml of acetone is homogeneously mixed with 99 g of a carrier for a mosquito-coil (mixture of Tabu powder, Pyrethrum marc and wood powder at the ratio of 5:3:2) and 120 ml of water dissolving 0.3 g of Malachite Green and 0.2 g of sodium dehydroacetate therein. The mixture is kneaded sufficiently, molded and dried to give mosquito-coil.

Preparation Example 21

Acetone is added to 0.2 g of the Pyrone Compound, 0.1 g of BHT and 0.4 g of piperonyl butoxide to make the total 10 ml. A half milliliter (0.5 ml) of the obtained solution is impregnated with a base material (a plate of compacted fibrils of a mixture of pulp and cotton linters: 2.5 cm×1.5 cm, 0.3 cm in thickness) for mosquito-mat homogeneously to give a mosquito-mat for electric heater.

Preparation Example 22

One-fifth part (0.2 part) of the Pyrone Compound and 0.1 part of BHT are dissolved in 99.7 parts of deodorized kerosene to give a solution. The solution is charged in a vessel of polyvinyl chloride. In the vessel is inserted an absorptive wick which is inorganic powder solidified with a binder and then calcined, the upper portion of which wick can be heated with a heater, to give a part of electric heating fumigation device using a liquid.

Preparation Example 23

A solution prepared by dissolving 100 mg of the Pyrone Compound in an appropriate amount of acetone is impregnated with a porous ceramic plate (4.0 cm×4.0 cm, 1.2 cm in thickness) to give a heating fumigant.

Preparation Example 24

A solution prepared by dissolving 500 mg of the Pyrone Compound in 2.5 ml of acetone is impregnated with a porous ceramic plate (4.2 cm×4.2 cm, 1.2 cm in thickness, having 102 holes of 3 mm in diameter) to give a heating fumigant.

Preparation Example 25

Seven parts of ethyl oleate, 0.5 part of zinc oxide, 2 parts of α-starch and azodicarbonamide are mixed to make the total to 100 parts. Water is added to the mixture, followed by kneading, granulating with extruder and drying. Into 10 g of the obtained granules, a solution of 2.24 g of the Pyrone Compound dissolved in 2 ml of acetone is impregnated and dried to give a smoking.

In the following test examples, the compound of formula:

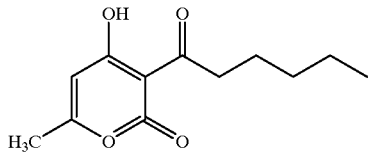

was used as Reference compound, which is described in Japanese Unexamined Patent Publication No. sho-51-19126.

Test Example 1

Ten (5 males and 5 females) adult houseflies (*Musca domestica*) were released in a glass chamber (70 cm cube, capacity: 0.34 m$^3$). Seven-tenth milliliter (0.7 ml) of the oil solution obtained in Preparation example 9 was applied into the chamber with a spray gun at a pressure of 0.9 kg/cm$^2$. Fifteen minutes after spraying, the knocked-down houseflies were counted. Reference compound was also tested.

The results are given in Table 1.

TABLE 1

| Tested compounds | Knock-down percentage (%) 15 min. after spraying |
| --- | --- |
| The Pyrone Compound | 95 |
| Reference compound | 0 |

Test Example 2

The same procedure was performed as in Test example 1 except that ten female adult common mosquitoes (*Culex pipiens pallens*) in place of houseflies were used. As a result of two repetitions, the knock-down percentage at 15 minutes after spraying was 100%.

Test Example 3

A square of paper (side: 20 cm) was covered on the iron net set on the bottom of the metallic chamber (46 cm×46 cm, 70 cm in height). A container (8.75 cm in diameter, 7.5 cm in height, having 16-mesh net at the bottom and spreading butter on the wall for preventing escape) was set on the paper. In the container, ten (5 males and 5 females) adult German cockroaches (*Blattella germanica*) were released. By means of spray gun, 1.5 ml of the oil solution obtained in Preparation example 9 was applied to the test insects at a pressure of 0.42 kg/cm$^2$ from the upper part of the chamber. The container was taken out of the chamber 30 seconds after spraying and the test insects were transferred to a clean plastic cup. One minute after spraying, the knocked-down cockroaches were counted. As a result, the knock-down percentage was 100%. Reference compound was also tested and the knock-down percentage was 42%.

Test Example 4

In a test chamber of 3 m×4 m and 2.3 m in height (28 m$^3$), two plastic cups were put at two corners, wherein each cup has ten (5 males and 5 females) adult German cockroaches (*Blattella germanica*) therein. Ten grams (10 g) of the smoking obtained in Preparation example 25 and 50 g of magnesium oxide were charged into each of the cells in an aluminum container having an aluminum wall. The cell charged magnesium oxide has small holes. The aluminum container was dipped into water in the plastic container set in the test chamber. The smoking was heated to release the vaporized active ingredient by the reaction heats of magnesium oxide with water. After 2 hours, knock-down percentage was observed. Further, the cockroaches were transferred to a clean plastic cup and given foods and water. The mortality was observed after 7 days.

Furthermore, the same tests were performed except that six (3 males and 3 females) adult smokybrown cockroaches (*Periplaneta fuliginosa*) and six (3 males and 3 females) adult American cockroaches (*Periplaneta americana*) were used in place of ten German cockroaches. The results are given in Table 2.

TABLE 2

| Tested cockroaches | Knock-down percentage (%) | Mortality (%) |
| --- | --- | --- |
| German cockroaches | 100 | 100 |
| smokybrown cockroaches | 100 | 100 |
| American cockroaches | 100 | 75 |

Test Example 5

On the bottom of a cubic chamber having 1.8 m of side (5.8 m$^3$), the heating fumigant (ceramic plate) obtained in Preparation example 24 with an electric heater was set in the center. Two plastic cups were put at two corners in the chamber, wherein each cup has ten (5 males and 5 females) adult German cockroaches (*Blattella germanica*) therein. Two hours after turning on an electric current, the ceramic plate was heated to about 200° C. (200±5° C.) and the active ingredient was vaporized. The heating temperature was estimated by measuring a surface temperature of the ceramic plate with radiation pyrometer (TR-0506C produced by Minolta Company) in advance. Then, the knocked-down cockroaches were counted and the knock-down percentage was calculated. Further, the cockroaches were transferred to a clean plastic cup and given foods and water. The mortality was observed after 7 days.

Furthermore, the same tests were performed except that six (3 males and 3 females) adult smokybrown cockroaches (*Periplaneta fuliginosa*) and six (3 males and 3 females) adult American cockroaches (*Periplaneta americana*) were used in place of ten German cockroaches. The results are given in Table 3.

TABLE 3

| Tested cockroaches | Knock-down percentage (%) | Mortality (%) |
| --- | --- | --- |
| German cockroaches | 100 | 100 |
| smokybrown cockroaches | 100 | 83 |
| American cockroaches | 100 | 67 |

Test Example 6

On the bottom center of a cubic chamber having 70 cm of side (0.34 m$^3$), the mosquito-coil obtained in Preparation example 18 was set in a mosquito-coil holder. The mosquito-coil was ignited and the air in the chamber was stirred with a battery-type small electric fun. After that, the mosquito-coil and the electric fun were taken out and twenty female adult common mosquitoes (*Culex pipiens pallens*) were released into the chamber. After 15 minutes, the knock-down percentage was observed. Reference compound was also tested. The results are given in Table 4.

TABLE 4

| Tested compounds | Knock-down percentage (%) |
| --- | --- |
| The Pyrone Compound | 98 |
| Reference compound | 8 |

Test Example 7

A designated amount of the Pyrone Compound was dissolved in acetone to give a 0.2 ml solution, which was uniformly treated on a filter paper having 3.8 cm in diameter, and air-dried for one hour. The filter paper was filled in a lid of a 200 ml glass bottle. Twenty adult cat fleas (*Ctenocephalides felis*) were released in the glass bottle, which was followed by covering with the lid. The glass bottle was upset for making the fleas contact with the filter paper, and kept at room temperature (25±3° C.) for one day. After that, the mortality was observed. The tests were repeated three times and the results are given in Table 5.

TABLE 5

| Dosage | 200 mg/m$^2$ | 800 mg/m$^2$ |
| --- | --- | --- |
| Mortality (%) | 98 | 100 |

Test Example 8

A designated amount of the Pyrone Compound was dissolved in acetone to give a 0.2 ml solution, which was uniformly treated on a filter paper having 3.8 cm in diameter, and air-dried for one hour. The filter paper was set on an aluminum plate of 4 cm in diameter. Twenty cat flea (*Ctenocephalides felis*) eggs were put on the filter paper and the plate was kept at 25±3° C. and 70–90% of humidity in a plastic Petri dish. After 7 days, the hatching was observed. The tests were repeated three times and the results are given in Table 6.

TABLE 6

| Dosage | 5 mg/m$^2$ | 25 mg/m$^2$ | 125 mg/m$^2$ |
| --- | --- | --- | --- |
| Hatching ratio (%) | 1.7 | 0 | 0 |

Test Example 9

The Pyrone Compound was dissolved in water to give a 10 ml solution having 0.5% (w/w) of a concentration. The solution was mixed with 200 g of soil and air-dried. After keeping for 3 months at 40° C. and in the dark, about 10 g of the soil were put on a plastic Petri dish having 9 cm in diameter. The soil was wetted with distilled water and 10 termites (*Coptotermes formosanus*) were released thereon. After 10 days, the termites were observed and the percent moribund was 100%.

Test Example 10

On a black drawing paper having 38 mm in diameter, 0.2 ml of an acetone solution of the Pyrone Compound was added dropwise and air-dried. The treated dosage was 800 mg/m$^2$. The drawing paper was set on an aluminum plate having 38 mm in diameter and adhesives were put on the edge to prevent for tested mites to escape. About 30 adult American house dust mites (*Dermatophagoides farinae*) were released on the drawing paper and kept at 25° C. and 65% of humidity for 24 hours. After that, the mortality was observed. The result was 100%.

Test Example 11

On a black drawing paper having 38 mm in diameter, 0.2 ml of an acetone solution of the Pyrone Compound was added dropwise and air-dried. The treated dosage was 800 mg/m$^2$. The drawing paper was set on an aluminum plate having 38 mm in diameter and adhesives were put on the edge to prevent for tested mites to escape. About 30 adult copra mites (*Tyrophagus putrescentiae*) were released on the drawing paper and kept at 25° C. and 75% of humidity for 24 hours. After that, the mortality was observed. The result was 93%.

Test Example 12

According to Preparation examples 10–14, 1.0% oil-based aerosol of the Pyrone Compound was obtained. A container (8.75 cm in diameter, 7.5 cm in height, bottom covered 16-mesh iron net and inside wall painted butter for preventing tested pill bugs to escape) having 5 adult pill bugs (*Armadillidium vulgare*) therein was set on the bottom center of a glass cylinder having 20 cm in diameter and 60 cm in height. About 450 mg of the above oil-based aerosol were sprayed to the pill bugs from the upper part of the cylinder. After 30 seconds, the pill bugs were taken out and put into a clean plastic cup having soil and dead leaves therein. The pill bugs were given food and water and observed after 3 days. The tests were repeated twice. The mortality was 100%. Reference compound was also tested and the mortality was 40%.

Test Example 13

The same procedure was performed as in Test example 12 except that 5 adult *Porcellio scaber* were used in place of *Armadillidium vulgare*. As a result, the mortality of the Pyrone Compound was 100%.

Test Example 14

According to Preparation examples 10–14, 1.0% oil-based aerosol of the Pyrone Compound was obtained. In a 200 cc plastic cup having inside wall painted talc for preventing tested ants to escape, about 30 g of soil were set and 10 ants (*Formica japonica*) were release thereon. The plastic cup was set on the bottom center of a glass cylinder having 20 cm in diameter and 60 cm in height. About 450 mg of the above oil-based aerosol were sprayed to the ants from the upper part of the cylinder. After 10 seconds, the ants were taken out and put into a clean plastic cup having a piece of watermelon peel as food therein. After 2 days, the mortality was observed and the result was 70%.

Test Example 15

About 30 cotton aphids (*Aphis gossypii*) were put on a cucumber leaf (in first-leaf stage) grown in a 90 ml plastic cup.

Next day, the formulation obtained in Preparation example 7 was diluted with water containing a spreading agent (Tokurino produced by Nihon Nohyaku Co.) to make the concentration of the Pyrone Compound to 500 ppm. Thirty milliliters (30 ml) of the dilution were sprayed to the cucumber and air-dried. The plastic pot was put in a container and allowed to stand at 22±2° C. in a greenhouse. After 6 days, the mortality was 90% or more.

Test Example 16

About 50 whiteflies (*Bemisia argentifolii*) were put on a cabagge leaf (in first-leaf stage) grown in a 90 ml plastic cup.

The formulation obtained in Preparation example 7 was diluted with water containing a spreading agent (Tokurino produced by Nihon Nohyaku Co.) to make the concentration of the Pyrone Compound to 500 ppm. Thirty milliliters (30 ml) of the dilution were sprayed to the cabbage (in first-leaf stage) and air-dried. The plastic pot was allowed to stand at 25±2° C. in a greenhouse. After 6 days, the mortality was 90% or more.

Test Example 17

A methanol solution (50 μg/20 μl) of the Pyrone Compound was prepared. The solution (20 μl) was painted on a cut leaf disc of cabbage (1 cm in diameter). After vaporizing methanol, the leaf disc was put on a filter paper, which was wet with 1 ml of water, in Petri dish making the painted surface upside. Two 4-instar larvae of tobacco cutworm (*Spodoptera litura*) were put in the Petri dish. After 24 hours, the damage of the leaf disc was observed and compared with the test result of the non-treated disc. The tests were repeated 5 times. As a result, the damage was clearly smaller comparing with the non-treated disc.

Test Example 18

The same procedure was performed as in Test example 17 except that five 3-instar larvae of diamondback moth (*Plutella xylostella*) was used in place of tobacco cutworm (*Spodoptera litura*). As a result, the damage was clearly smaller comparing with the non-treated disc.

Test Example 19

The formulation obtained in Preparation example 2 was diluted with water to make the concentration of the Pyrone Compound to 500 ppm. One milliter (1 ml) of the dilution was added to 6 g of artificial food (Insecta LF produced by Nihon Nosankogyo Co.) in plastic cup having 5.5 cm in diameter. Thirty first-instar larvae of summer fruit tortrix (*Adoxophyes orana fasciata*) were put into the plastic cup. After 6 days, the mortality was 90% or more.

Test Example 20

The formulation obtained in Preparation example 2 was diluted with water to make the concentration of the Pyrone Compound to 500 ppm. One milliliter (1 ml) of the dilution was added to 6 g of artificial food (Insecta LF produced by Nihon Nosankogyo Co.) in plastic cup having 5.5 cm in diameter. About 50 eggs of peach fruit moth (*Carposina niponensis*) laid on nylon cloth were put into the plastic cup. After 10 days, the ovicidal effect was 90% or more.

Test Example 21

In a test chamber of 3 m×4 m and 2.3 m in height (28 m³), two plastic cups were put at two corners, wherein each cup has ten (5 males and 5 females) adult German cockroaches (*Blattella germanica*) therein. The formulation obtained in Preparation example 16 was set in the center of the bottom and the contents of the aerosol were totally released. After 2 hours, the knock-down percentage was 100%.

Test Example 22

According to Preparation examples 10–14, 1.0% oil-based aerosol of the Pyrone Compound was obtained. A container (12.5 cm in diameter, 17.5 cm in height, bottom covered 16-mesh iron net and inside wall painted butter for preventing tested pill bugs to escape) having a centipede (*Scolopendra subspinipes mutilans*) therein was set on the bottom center of a glass cylinder having 20 cm in diameter and 60 cm in height. About 1000 mg of the above oil-based aerosol were sprayed to the centipede from the upper part of the cylinder. After 30 seconds, the centipede was taken out and put into a clean plastic cup and given food and water. It was observed that the centipede was dead after 3 days.

What is claimed is:

1. A method for controlling arthropods which comprises applying an effective amount of an α-pyrone compound shown by the formula:

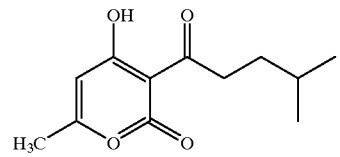

to arthropods or a place where arthropods inhabit.

2. A method according to claim 1, wherein the arthropods are houseflies.

3. A method according to claim 1, wherein the arthropods are mosquitoes.

4. A method according to claim 1, wherein the arthropods are cockroaches.

5. A method according to claim 1, wherein the arthropods are fleas.

6. A method according to claim 1, wherein the arthropods are termites.

7. A method according to claim 1, wherein the arthropods are house dust mites.

8. A method according to claim 1, wherein the arthropods are pill bugs.

9. A method according to claim 1, wherein the arthropods are ants.

10. A method according to claim 1, wherein the arthropods are aphids.

11. A method according to claim 1, wherein the arthropods are whiteflies.

12. A method according to claim 1, wherein the arthropods are lepidopterous insects.

13. A method according to claim 1, wherein the arthropods are millipedes or centipedes.

* * * * *